(12) United States Patent
Baril et al.

(10) Patent No.: US 11,730,533 B2
(45) Date of Patent: *Aug. 22, 2023

(54) AUXILIARY ELECTROSURGICAL RETURN RIVET FOR USE WITH CUTTING GUARD

(71) Applicant: Covidien LP, Mansfield, MA (US)

(72) Inventors: Jacob C. Baril, Norwalk, CT (US); Justin J. Thomas, New Haven, CT (US); Saumya Banerjee, Hamden, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 456 days.

This patent is subject to a terminal disclaimer.

(21) Appl. No.: 16/900,230

(22) Filed: Jun. 12, 2020

(65) Prior Publication Data
US 2021/0386470 A1 Dec. 16, 2021

(51) Int. Cl.
*A61B 18/12* (2006.01)
*A61B 18/16* (2006.01)
(Continued)

(52) U.S. Cl.
CPC .......... *A61B 18/1233* (2013.01); *A61B 18/16* (2013.01); *A61B 2018/00077* (2013.01); *A61B 2018/126* (2013.01); *A61B 2018/1405* (2013.01)

(58) Field of Classification Search
CPC ............ A61B 18/1233; A61B 18/1402; A61B 18/1482; A61B 18/16; A61B 2018/00077;
(Continued)

(56) References Cited

U.S. PATENT DOCUMENTS 4,237,886 A * 12/1980 Sakurada ................. A61N 1/04
252/511
5,312,391 A 5/1994 Wilk
(Continued)

FOREIGN PATENT DOCUMENTS

WO 0101846 A2 1/2001
WO 2016014589 A1 1/2016

OTHER PUBLICATIONS

U.S. Appl. No. 16/776,922, filed Jan. 30, 2020, Inventor: Jacob Baril.
(Continued)

*Primary Examiner* — Khadijeh A Vahdat
(74) *Attorney, Agent, or Firm* — Carter, DeLuca & Farrell LLP

(57) ABSTRACT

An auxiliary return system for use with a bipolar electrosurgical device includes a tissue guard defining open proximal and distal ends and a body extending therebetween. The body includes outer and inner peripheral surfaces, the inner peripheral surface defining a lumen extending between the open proximal and distal ends, the outer peripheral surface including an elongated channel defined therein configured to receive a ground wire, a distal end of the elongated channel includes a pocket defined between the inner and outer peripheral surfaces of the body. An electrically conductive rivet includes a proximal end configured to engage the inner peripheral surface of the body and a distal end configured to engage the outer peripheral surface of the body to secure the rivet within the pocket. The distal end including a connector configured to engage the ground wire to provide electrical continuity between the ground wire and the rivet.

10 Claims, 5 Drawing Sheets

(51) Int. Cl.
*A61B 18/14* (2006.01)
*A61B 18/00* (2006.01)

(58) Field of Classification Search
CPC .... A61B 2018/00601; A61B 2018/126; A61B 2018/1405; A61B 2018/1412; A61B 2018/167
See application file for complete search history.

(56) References Cited

U.S. PATENT DOCUMENTS

| | | | |
|---|---|---|---|
| 5,403,311 A | 4/1995 | Abele et al. | |
| 5,458,598 A | 10/1995 | Feinberg et al. | |
| 5,556,397 A | 9/1996 | Long et al. | |
| 5,633,578 A | 5/1997 | Eggers et al. | |
| 5,814,044 A | 9/1998 | Hooven | |
| 5,919,202 A | 7/1999 | Yoon | |
| 6,086,583 A | 7/2000 | Ouchi | |
| 6,113,596 A | 9/2000 | Hooven et al. | |
| 6,379,350 B1 | 4/2002 | Sharkey et al. | |
| 6,387,094 B1 | 5/2002 | Eitenmuller | |
| 6,440,138 B1 | 8/2002 | Reiley et al. | |
| 6,565,560 B1 | 5/2003 | Goble et al. | |
| 7,041,101 B2 | 5/2006 | Eggers | |
| 7,232,440 B2 | 6/2007 | Dumbauld et al. | |
| 7,241,294 B2 | 7/2007 | Reschke | |
| 7,303,559 B2 | 12/2007 | Peng et al. | |
| 7,510,562 B2 | 3/2009 | Lindsay | |
| 7,537,594 B2 | 5/2009 | Sartor | |
| 7,588,570 B2 | 9/2009 | Wakikaido et al. | |
| 7,935,109 B2 | 5/2011 | Cosmescu | |
| 8,267,928 B2 | 9/2012 | Orszulak et al. | |
| 8,328,804 B2 | 12/2012 | Heard et al. | |
| 8,454,600 B2 | 6/2013 | Huseman | |
| 8,636,734 B2 | 1/2014 | Burbank et al. | |
| 8,753,341 B2 | 6/2014 | Landry et al. | |
| 8,808,287 B2 | 8/2014 | Heard et al. | |
| 2002/0049442 A1 | 4/2002 | Roberts et al. | |
| 2005/0187547 A1 | 8/2005 | Sugi | |
| 2006/0095027 A1 | 5/2006 | Eggers | |
| 2008/0015563 A1 | 1/2008 | Hoey et al. | |
| 2009/0254084 A1 | 10/2009 | Naito | |
| 2013/0178852 A1 | 7/2013 | Allen, IV et al. | |
| 2013/0267947 A1 | 10/2013 | Orszulak | |
| 2014/0031715 A1 | 1/2014 | Sherar et al. | |
| 2016/0058495 A1 | 3/2016 | Twomey | |

OTHER PUBLICATIONS

U.S. Appl. No. 16/540,593, filed Aug. 14, 2019, Inventor: Jacob C. Baril et al.
U.S. Appl. No. 16/781,557, filed Feb. 4, 2020, Inventor: Jacob C. Baril.
U.S. Appl. No. 16/789,553, filed Feb. 13, 2020, Inventor: Jacob C. Baril et al.

* cited by examiner

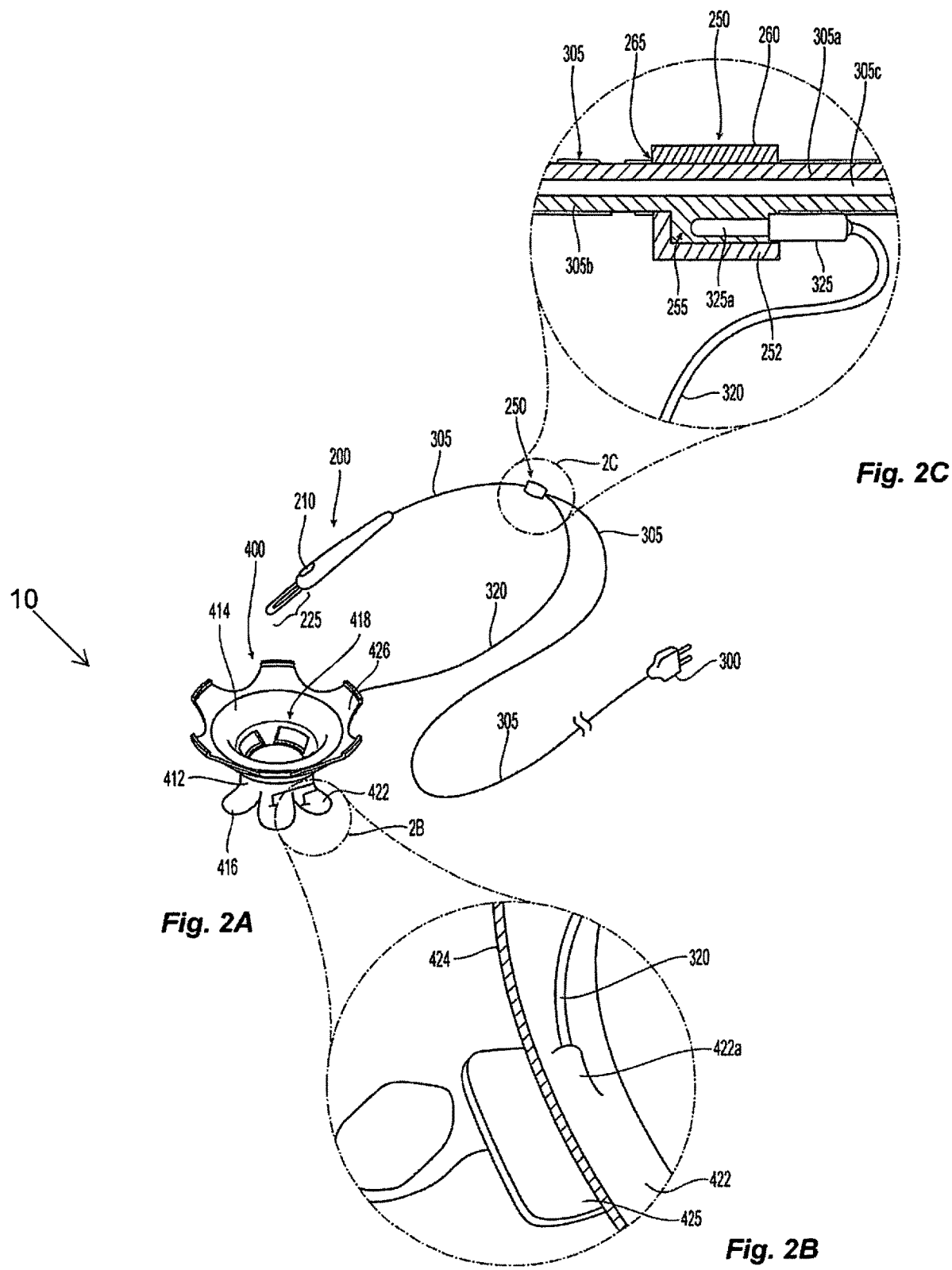

AUXILIARY ELECTROSURGICAL RETURN RIVET FOR USE WITH CUTTING GUARD

FIELD

The present disclosure relates to tissue specimen removal and, more particularly, to tissue guards and systems incorporating the same for use in tissue specimen removal procedures and other electrosurgical surgical procedures.

BACKGROUND

In minimally invasive surgical procedures, operations are carried out within an internal body cavity through small entrance openings in the body. The entrance openings may be natural passageways of the body or may be surgically created, for example, by making a small incision into which a cannula is inserted.

Minimally invasive surgical procedures may be used for partial or total removal of tissue from an internal body cavity. However, the restricted access provided by minimally invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity. Typically, electrosurgical instruments such as bipolar electrosurgical pencils may be utilized for this purpose.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is an auxiliary return system for use with a bipolar electrosurgical device which includes a tissue guard having an open proximal end, an open distal end, and a body extending between the open proximal end and the open distal end. The body includes an outer peripheral surface and an inner peripheral surface defining a lumen extending between the open proximal end and the open distal end. The outer peripheral surface includes an elongated channel defined therein configured to receive a ground wire therein. A distal end of the elongated channel includes a pocket defined between the inner peripheral surface and the outer peripheral surface of the body. An electrically conductive rivet is included having proximal and distal ends, the proximal end of the rivet configured to engage the inner peripheral surface of the body and the distal end of the rivet configured to engage the outer peripheral surface of the body to secure the rivet within the pocket. The distal end of the rivet includes an electrical connector configured to electrically and mechanically engage the ground wire to provide electrical continuity between the ground wire and the rivet.

In aspects according to the present disclosure, the proximal end and the distal end of the rivet are two different sizes. In other aspects according to the present disclosure, the proximal end of the rivet includes a large cap-like head to facilitate grounding of an electrosurgical device within the lumen. In yet other aspects according to the present disclosure, the distal end of the rivet includes a through hole for engaging the ground wire. In still other aspects according to the present disclosure, the distal end of the rivet is crimped to secure the ground wire therein.

In aspects according to the present disclosure, the ground wire electrically couples at a first end to the rivet and a second end of the ground wire is adapted to electrically engage a return from an electrosurgical device thereby providing electrical continuity between the rivet and the return. In other aspects according to the present disclosure, the electrosurgical device is an electrosurgical pencil. In yet other aspects according to the present disclosure, the distal end of the body is oblong and includes a long petal and a short petal.

In aspects according to the present disclosure, the elongated channel defined in the body provides rigidity to the longer petal of the body of the tissue guard. In other aspects according to the present disclosure, the elongated channel defined in the body is formed by adding a material atop the body having a higher durometer rating.

Provided in accordance with other aspects of the present disclosure is an auxiliary return system for use with a bipolar electrosurgical device which includes a tissue guard defining an open proximal end, an open distal end, and a body extending between the open proximal end and the open distal end. The body includes an outer peripheral surface and an inner peripheral surface defining a lumen extending between the open proximal end and the open distal end. An electrically conductive rivet is included that has proximal and distal ends, the proximal end of the rivet configured to engage the inner peripheral surface of the body and the distal end of the rivet configured to engage the outer peripheral surface of the body to secure the rivet to the body. The distal end of the rivet includes an electrical connector configured to electrically and mechanically engage the ground wire to provide electrical continuity between the ground wire and the rivet.

In aspects according to the present disclosure, the proximal end of the rivet includes a large cap-like head to facilitate grounding of an electrosurgical device within the lumen. In other aspects according to the present disclosure, the distal end of the rivet includes a through hole for engaging the ground wire. In yet other aspects according to the present disclosure, the distal end of the rivet is crimped to secure the ground wire therein.

In aspects according to the present disclosure, the ground wire electrically couples at a first end to the rivet and a second end of the ground wire is adapted to electrically engage a return from an electrosurgical device thereby providing electrical continuity between the rivet and the return. In other aspects according to the present disclosure, the electrosurgical device is an electrosurgical pencil. In still other aspects according to the present disclosure, the distal end of the body is oblong and includes a long petal and a short petal.

Provided in accordance with other aspects of the present disclosure is a method for providing an auxiliary return for a tissue guard that includes: inserting an electrically conductive rivet through a body of a tissue guard such that a proximal end of the rivet engages against an inner peripheral surface of the body and a distal end of the rivet engages an outer peripheral surface of the body; feeding an exposed end of a ground wire from an electrical return through a wire hole defined in the distal end of the rivet; and crimping the distal end of the rivet to secure the exposed end of the ground wire therein and secure the rivet to the body.

Provided in accordance with other aspects of the present disclosure is a method for providing an auxiliary return for a tissue guard that includes: inserting an electrically conductive rivet through a body of a tissue guard such that a proximal end of the rivet securely engages against an inner peripheral surface of the body and a distal end of the rivet securely engages an outer peripheral surface of the body; and electrically engaging the rivet with a ground wire from an electrical return.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

FIG. 2A a schematic view of an electrical return system for use with a tissue guard and electrosurgical bipolar pencil in accordance with the present disclosure;

FIG. 2B is an enlarged view of the area of detail of FIG. 2A;

FIG. 2C is an enlarged view of the area of detail of FIG. 2A;

DETAILED DESCRIPTION

Figure 1A:
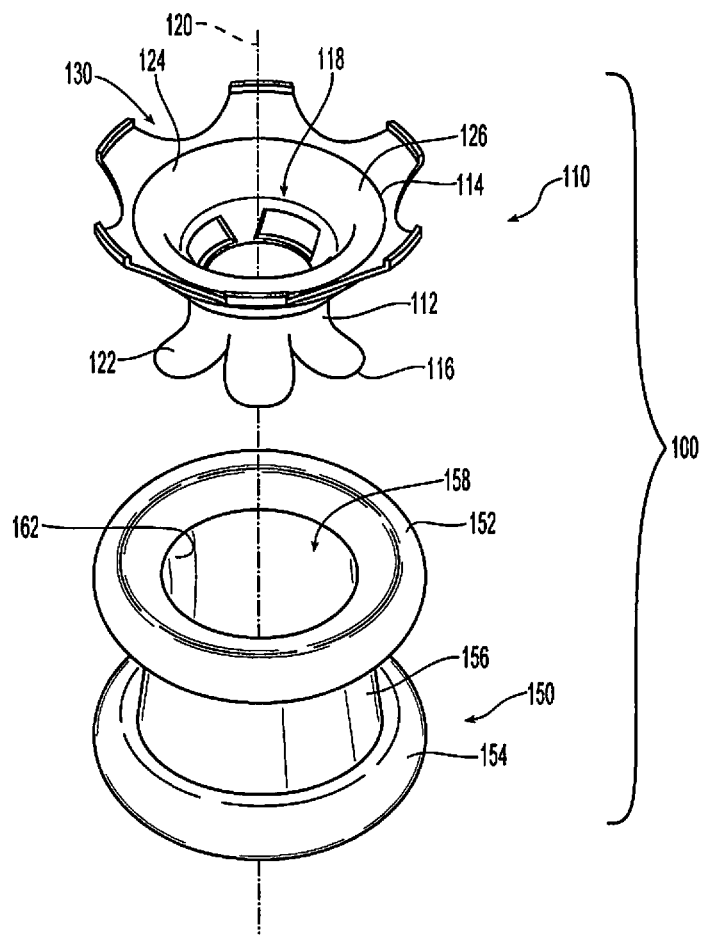
FIG. 1A is an exploded, top, perspective view of a prior art an access device and a tissue guard.
Figure 1B:
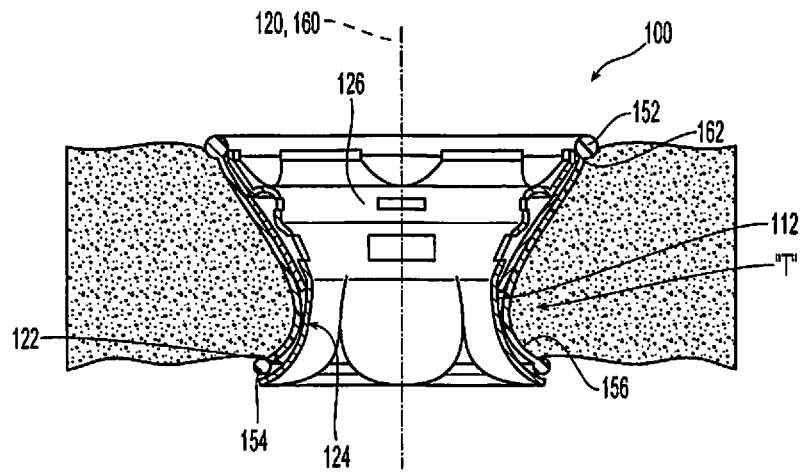
FIG. 1B is a cross-sectional view of the access device and tissue guard of FIG. 1A shown assembled and disposed within an opening in tissue.

Turning to FIGS. 1A and 1B, a prior art system 100 is shown and includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration. One or more flanges 126 are configured to secure the tissue guard to the access device 150.

Access device 150 may be configured as a tissue retractor, an access port, or other suitable access device configured for positioning within an opening in tissue "T," e.g., a surgical incision or a naturally occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 may further define an inwardly extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Turning now to FIGS. 2A-2C, an auxiliary electrical return system for use with a tissue guard and bipolar electrosurgical pencil is shown and is generally identified as system 10. System 10 includes a cutting or tissue guard 400 and an electrosurgical pencil 200. Tissue guard 400 is similar to tissue guard 110 described above and, as such, only those elements that differ are described in detail below. Bipolar electrosurgical pencil 200 is only generally described herein and only those features necessary for an understanding of the system 10 are provided in detail. Cross reference is made to various bipolar electrosurgical pencils that may be utilized with system 10, for example, U.S. patent application Ser. No. 16/776,922 filed Jan. 30, 2020, U.S. patent application Ser. No. 16/540,593 filed Aug. 14, 2019, U.S. patent application Ser. No. 16/781,557 filed Feb. 4, 2020 and U.S. patent application Ser. No. 16/789,553 filed Feb. 13, 2020, the entire contents of each of which being incorporated by reference herein.

Tissue guard 400 includes a proximal rim 414 which is configured for engagement with an access device, for example, access device 150, an elongated body portion 412 and a distal end 416 configured for insertion within the access device 150. One or more flanges 426 are configured to engage the proximal rim 152 of the access device 150 to secure the tissue guard 400 therein. An outer surface 422 of the tissue guard 400 abuts the inner peripheral surface of the access device 150 in situ.

FIG. 2B shows an enlarged view of the distal end 416 of the tissue guard 400 wherein an electrical ground plate 425 is disposed on an inner peripheral surface 424 thereof in communication with inner lumen 418. The outer surface 422 of tissue guard 400 includes a pocket 422a defined therein configured to receive a ground wire 320 for ultimate connection at one end to the ground plate 425 and the other end to a banana plug 325 (or the like) that operably connects to an auxiliary coupling 250. Ground wire 320 provides electrical continuity between the coupling 250 and the ground plate 425. Ground plate 425 acts as an auxiliary ground return for the electrosurgical pencil 200 during use as explained in more detail below.

Electrosurgical pencil 200, in general, includes an end effector 225 attached at a distal end thereof that includes a bipolar electrical arrangement for treating tissue within the access device 150 (and tissue guard 400). Pencil 200 includes an electrical cable 305 attached at proximal end thereof which is configured to provide an active lead 305a to one electrode on the end effector 225 and a ground lead 305b on the other electrode on the end effector 225. The cable 305 is also configured to carry a switch lead 305c that connects to the pencil switch 210 for activation.

Coupling 250 includes a housing 260 having an inner bore 265 defined therein configured to receive cable 305 therethrough which ultimately connects to a plug 300 for connection to an electrosurgical generator (not shown). A flange 252 is configured to extend from the coupling 250 proximate the ground lead 305b within cable 305 and defines a plug receptacle 255 therein configured to operably receive banana plug 325 (or the like) for connection to ground wire 320 and, ultimately, to ground plate 425 as described above. Ground lead 305b electrically connects to ground wire 330 via the banana plug 325 to provide the same polarity to ground plate 425 as the return electrode in the end effector 225. As a result, the ground plate 425 acts as a secondary or auxiliary electrical return during use of the bipolar pencil 200.

In embodiments, any electrosurgical pencil 200 may be retrofitted with the coupling 250 to provide the auxiliary return. For example, the coupling 250 may include an IDC fitting (or the like) that is configured to operably engage the ground lead 305b in cable 305 in a snap fit manner. The IDC fitting includes the plug receptacle 255 that operable couples to the banana plug 325 from the ground wire 320. In this fashion, the electrosurgical pencil 200 is now configured with an auxiliary or secondary return.

FIGS. 3A-3D show an alternate tissue guard 500 for use with system 10. Tissue guard 500 includes a body 512 having a proximal end 514 and a distal end 516 configured for use with an access device 150 (as described above). Distal end 516 is generally oblong and includes a long petal 516a on one side thereof and a short petal 516b on an opposite side thereof to facilitate insertion of the tissue guard 500 into the access device 150 and an internal body cavity.

Figure 3A:
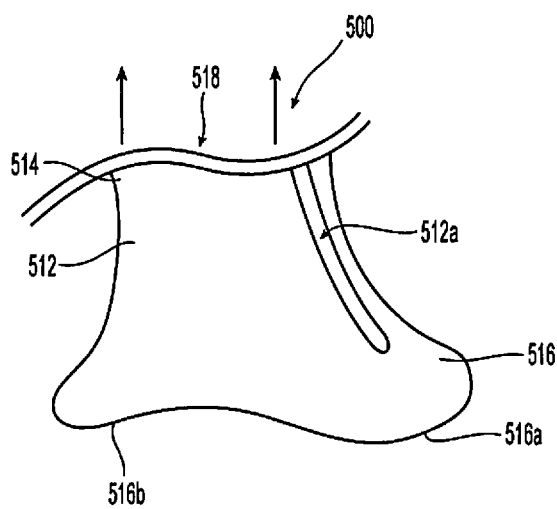
FIGS. 3A-3D show various views of another embodiment of an electrical return system for use with a tissue guard.
Figure 3B:
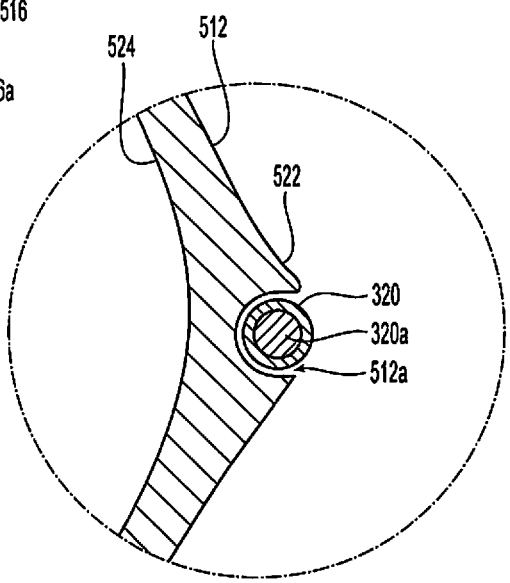
Figure 3C:
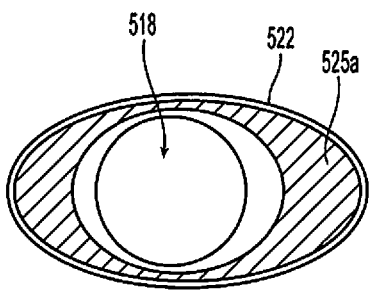
Figure 3D:
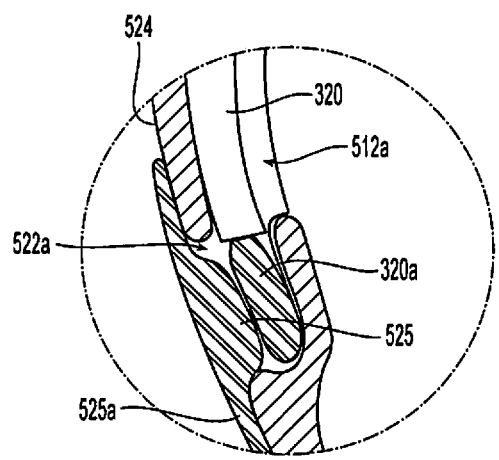

The outer peripheral surface 522 of the body 512 of the tissue guard 500 includes an elongated channel 512a defined therein and extending therealong from a point proximate the proximal end 514 to a point proximate the distal end 516 thereof (FIGS. 3A, 3C and 3D). Channel 512a is configured to receive and secure ground wire 320 therein. Channel 512a includes a pocket 522a at a distal end thereof that houses a wire connector 320a therein. Wire connector 320a is configured to operably and electrically connect to a distal end of the ground wire 320 (FIG. 3D).

Elongated channel 512a provide protection for the ground wire 320 and adds rigidity to the longer petal 516a which, in turn, facilitates insertion within the access device 150 and the surgical cavity. The elongated channel 512a may be created by adding material to the outer peripheral surface 522 to enhance robustness of the tissue guard 500. The added material may be made from a material having a higher durometer rating than the material used for the body 512 of the tissue guard 500.

Wire connector 320a is also disposed in electrical communication with a ground tab 525 disposed along an inner peripheral surface 524 of the lumen 518 of the body 512 and in general concentric registration with pocket 522a. Ground tab 525, in turn, is disposed in electrical communication with an inner conductive layer 525a deposited on a substantial portion of the inner peripheral surface of lumen 518 (FIG. 3C).

Inner conductive layer 525a may include a deposited return circuit layer (circuit formed by metal deposition technology or similar) or simply a layer of conductive material. The inner conductive layer 525a interfaces with the ground tab 525, which in turn, interfaces with the conductor 320a, which in turn, connects to the ground wire 320 which ultimately connects to the ground lead 305b from the electrosurgical device, e.g., pencil 200. As a result, the inner conductive layer 525a acts as a secondary or auxiliary electrical return during use of the electrosurgical device, e.g., pencil 200.

In embodiments, the electrically conductive layer 525a may be directly connected to the wire connector 320a eliminating the need for the ground tab 525. In this instance, during deposition, the inner conductive layer 525a is deposited on the inner periphery of the lumen 518 filling any void between the wire connector 320a within the pocket 522a.

Figure 4A:
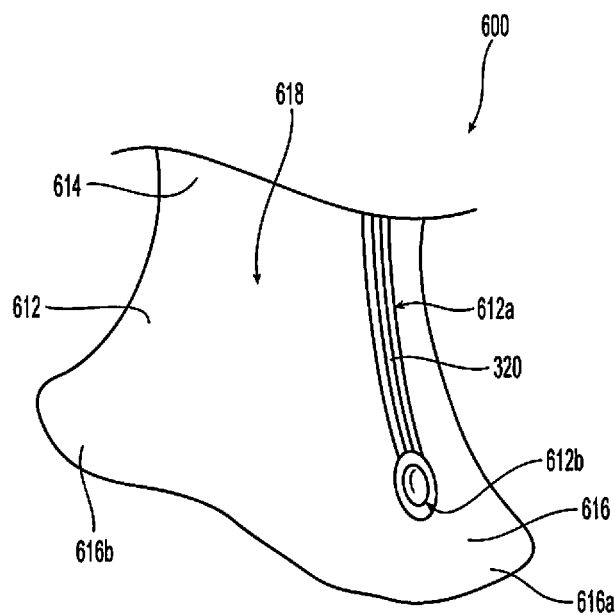
FIGS. 4A-4D show various views of another embodiment of an electrical return system for use with a tissue guard.

FIGS. 4A-4D show an alternate tissue guard 600 for use with system 10. Tissue guard 600 includes a body 612 having a proximal end 614 and a distal end 616 configured for use with an access device 150 (as described above). Much like the embodiment described above, distal end 616 is generally oblong and includes a long petal 616a on one side thereof and a short petal 616b on an opposite side thereof to facilitate insertion of the tissue guard 600 into the access device 150 and an internal body cavity (FIG. 4A).

The outer peripheral surface 622 of the body 612 of the tissue guard 600 includes an elongated channel 612a defined therein and extending therealong from a point proximate the proximal end 612 to a pocket 612b proximate the distal end 616 thereof (FIG. 4A). Channel 612a is configured to receive and secure ground wire 320 therein. Channel 612a includes the pocket 612b at a distal end thereof (FIG. 4D) that is configured to receive a rivet 700 for securing the ground wire 320 and for providing electrical continuity thereto as explained in more detail below.

Elongated channel 612a provide protection for the ground wire 320 and adds rigidity to the longer petal 616a which, in turn, facilitates insertion within the access device 150 and the surgical cavity. The elongated channel 612a may be created by adding material to the outer peripheral surface 622 to enhance robustness of the tissue guard 600. The added material may be made from a material having a higher durometer rating than the material used for the body 612 of the tissue guard 600.

FIG. 4A shows the ground wire 320 engaged within the elongated channel 612*a* with a distal end 320*a* of the ground wire 320 disposed proximate the pocket 612*b*. The elongated channel 612*a* may be configured to include a cross section that secures the ground wire 320 therein in a snap-fit or friction-fit manner.

Figure 4B:
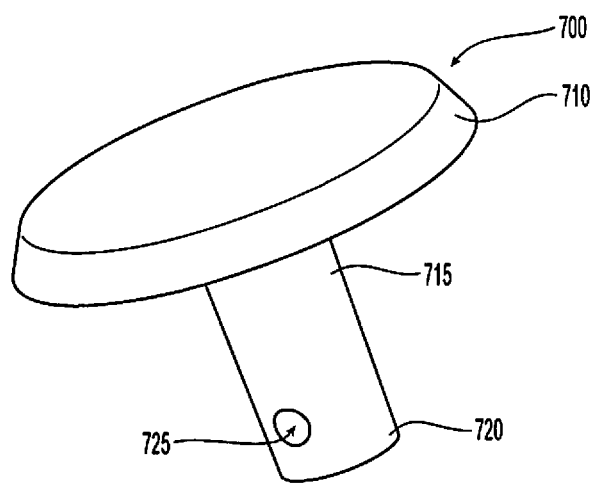
Figure 4C:
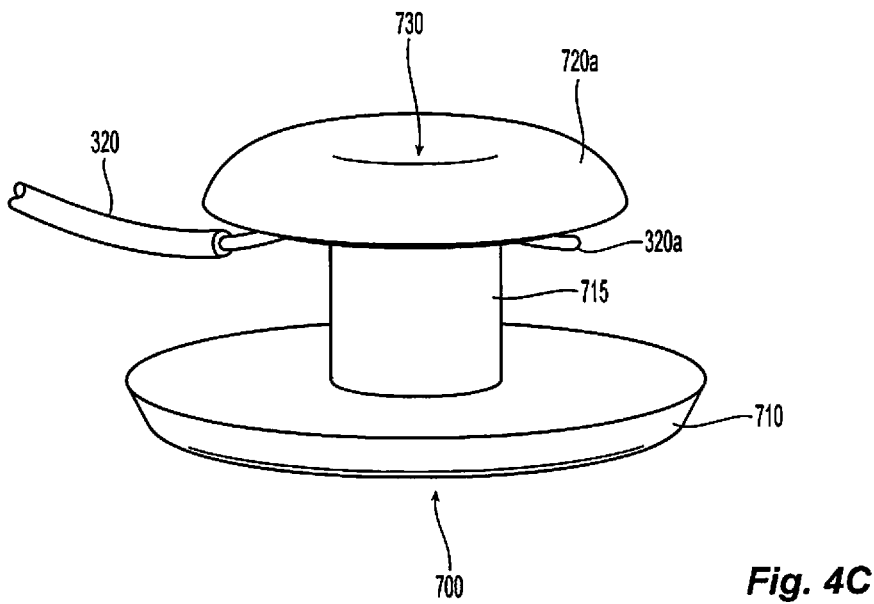
Figure 4D:
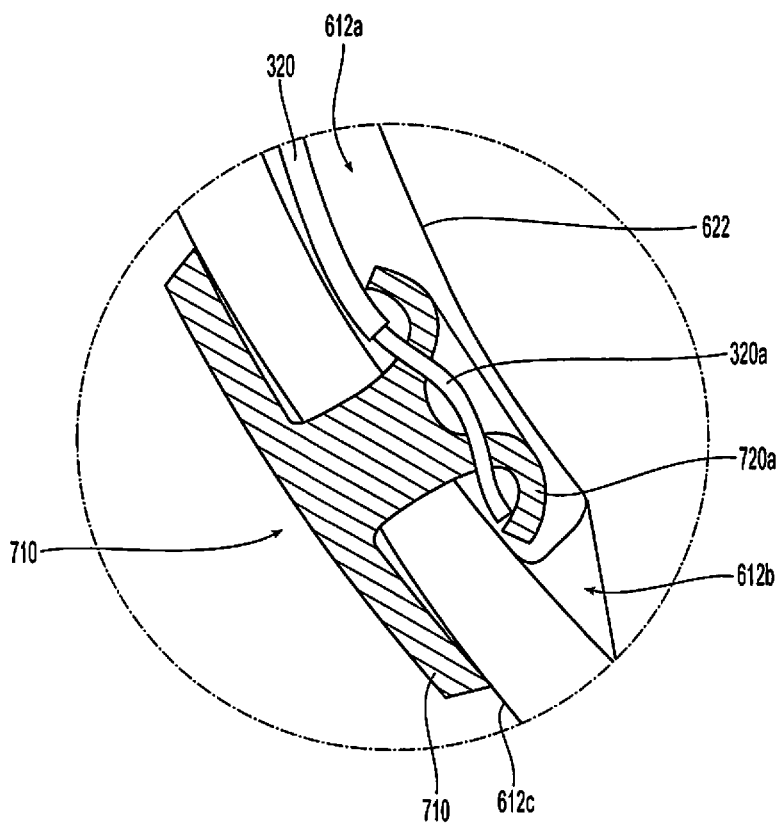

FIGS. 4B-4D show rivet 700 electrically connected to the ground wire 320 and placement of the rivet 700 within the tissue guard 600 for providing an electrical return. More particularly, rivet 700 includes a proximal 710, a distal end 720, and an elongated stem 715 disposed therebetween. Proximal end 710 is generally cap-like and includes a large head to insure both internal electrical continuity with the surgical instrument disposed within the tissue guard 600 and to properly seat and secure the distal end 720 of the rivet 700 within the pocket 612*b* (FIG. 4D).

Elongated stem 715 of rivet 700 includes a wire hole 725 configured to receive a distal exposed end 320*a* of the ground wire 320 therein. Wire hole 725 is defined proximate the distal end 720 of the rivet 700 to facilitate connection with the ground wire 320. More particularly and as best shown in FIGS. 4C and 4D, in order to connect the ground wire 320 to the rivet 700, the insulation of the ground wire 320 is stripped to expose the underlying conductive wire and then the exposed end 320*a* is inserted into wire hole 725 (FIG. 4C). Once inserted, the distal end 720 of the rivet 700 is crimped towards the proximal end 710 to secure the exposed end 320*a* of the ground wire 320 to the rivet 700 (FIG. 4D). This insures electrical connection between the two components.

Alternatively, the rivet 700 may include other types of connections to facilitate electrical connection, e.g., insulation displacement connectors (IDC) or insulation piercing connectors (IPC) or the like. IDC or IPC electrical connectors are designed to be connected to conductive wires of an insulated cable by a connection process which forces a sharpened blade (or blades) through the insulation upon engagement or insertion thereby bypassing the need to strip the wires from the insulation before connecting. Once inserted (or forcibly engaged), mechanical features of the IDC or IPC connector or electrical adhesives maintain the electrical connection with the newly exposed wire.

Rivet 700 is now electrically connected to the ground wire 320. The proximal end 710 of the rivet 700 is then buttoned through pocket 612*b* and an inner peripheral surface 612*c* of the lumen 618 of the body 612 in general concentric registration with pocket 612*b*. The large cap-like head of the proximal end 710 of rivet 700 secure the rivet 700 in place within the lumen 618 while the distal crimped end 720 anchors the rivet 700 in the pocket 612*b*. The large cap-like head of the proximal end 710 of rivet 700 now acts as a convenient auxiliary electrical ground return within the lumen 618 (FIG. 4D).

In embodiments, the ground connection may be made after the rivet 700 is positioned on the tissue guard 600. More particularly, the rivet 700 (shown in FIG. 4B) may be initially buttoned into the pocket 612*b* with the proximal end 710 against the inner peripheral surface 612*c* of lumen 618. A distal end 320*a* of the ground wire 320 may be stripped to expose the conductor and then inserted into the wire hole 725 (or an IDC or IPC (not shown) connector may be used). Once the exposed end 320*a* of the wire 320 is properly positioned, the distal end 720 of the rivet 700 is crimped to secure the ground wire 320 with rivet 700 and rivet 700 within pocket 612*b*.

The present disclosure also relates to a method for providing an auxiliary return for a tissue guard (e.g., tissue guard 600) that includes: inserting an electrically conductive rivet 700 through a body 612 of a tissue guard 600 such that a proximal end 710 of the rivet 700 engages against an inner peripheral surface 612*c* of the body 612 and a distal end 720 of the rivet 700 engages an outer peripheral surface 622 (or with the pocket 612*b*) of the body 612; feeding an exposed end 320*a* of a ground wire 320 from an electrical return through a wire hole 725 defined in the distal end 720 of the rivet 700; and crimping the distal end 720 of the rivet 700 to secure the exposed end 320*a* of the ground wire 320 therein and secure the rivet 700 to the body 612.

The present disclosure also relates to a method for providing an auxiliary return for a tissue guard 600 that includes: inserting an electrically conductive rivet 700 through a body 612 of a tissue guard 600 such that a proximal end 710 of the rivet 700 securely engages against an inner peripheral surface 612*c* of the body 612 and a distal end 720 of the rivet 700 securely engages an outer peripheral surface 622 (or within the pocket 612*b*) of the body 612; and electrically engaging the rivet 700 with a ground wire 320 from an electrical return.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An auxiliary return system for use with a bipolar electrosurgical device, comprising:
   a tissue guard defining an open proximal end, an open distal end, and a body extending between the open proximal end and the open distal end, the body including an outer peripheral surface and an inner peripheral surface defining a lumen extending between the open proximal end and the open distal end, the outer peripheral surface including an elongated channel defined within the outer peripheral surface and configured to receive a ground wire within the elongated channel, a distal end of the elongated channel including a pocket defined between the inner peripheral surface and the outer peripheral surface of the body, wherein the distal end of the body is oblong and includes a long petal and a short petal, wherein the elongated channel defined in the body provides rigidity to the long petal; and
   an electrically conductive rivet including proximal and distal ends, the proximal end of the rivet configured to engage the inner peripheral surface of the body and the distal end of the rivet configured to engage the outer peripheral surface of the body to secure the rivet within the pocket, the distal end of the rivet including an electrical connector configured to electrically and mechanically engage the ground wire to provide electrical continuity between the ground wire and the rivet.

2. The auxiliary return system according to claim 1, wherein the proximal end and the distal end of the rivet are two different sizes.

3. The auxiliary return system according to claim 1, wherein the proximal end of the rivet includes a large cap-like head to facilitate grounding of an electrosurgical device within the lumen.

4. The auxiliary return system according to claim 1, wherein the distal end of the rivet includes a through hole for engaging the ground wire.

5. The auxiliary return system according to claim 4, wherein the distal end of the rivet is crimped to secure the ground wire therein.

6. The auxiliary return system according to claim 1, wherein the ground wire electrically couples at a first end to the rivet and a second end of the ground wire is adapted to electrically engage a return from an electrosurgical device thereby providing electrical continuity between the rivet and the return.

7. The auxiliary return system according to claim 6, wherein the electrosurgical device is an electrosurgical pencil.

8. The auxiliary return system according to claim 1, wherein the body is made from a material having first durometer rating and the elongated channel defined in the body is formed by adding a material atop the body having a higher durometer rating than the first durometer rating.

9. An auxiliary return system for use with a bipolar electrosurgical device, comprising:
a tissue guard defining an open proximal end, an open distal end, and a body extending between the open proximal end and the open distal end, the body including an outer peripheral surface and an inner peripheral surface, the outer peripheral surface having an elongated channel defined in the outer peripheral surface, a portion of the elongated channel of the outer peripheral surface in communication with the inner peripheral surface, the elongated channel configured to receive a ground wire within the elongated channel, wherein the distal end of the body is oblong and includes a long petal and a short petal, wherein the elongated channel defined in the body provides rigidity to the long petal; and
an electrically conductive rivet including proximal and distal ends, the proximal end of the rivet configured to engage the inner peripheral surface of the body and the distal end of the rivet configured to engage the outer peripheral surface of the body to secure the rivet within the elongated channel, the distal end of the rivet including an electrical connector configured to electrically and mechanically engage the ground wire to provide electrical continuity between the ground wire and the rivet.

10. An auxiliary return system for use with a bipolar electrosurgical device, comprising:
a tissue guard including a body having an outer peripheral surface and an inner peripheral surface, the outer peripheral surface defining an elongated channel configured to receive a ground wire within the elongated channel, wherein a distal end of the body is oblong and includes a long petal and a short petal, wherein the elongated channel defined in the body provides rigidity to the long petal; and
an electrically conductive rivet including proximal and distal ends, the proximal end of the rivet configured to engage the inner peripheral surface of the body and the distal end of the rivet configured to engage the outer peripheral surface of the body to secure the rivet to the body, the distal end of the rivet including an electrical connector configured to electrically and mechanically engage a ground wire to provide electrical continuity between the ground wire and the rivet.

\* \* \* \* \*